United States Patent
Sattler

(10) Patent No.: US 8,206,648 B2
(45) Date of Patent: Jun. 26, 2012

(54) LIQUID CONTAINER WITH AN EXTRACTION CHIMNEY

(75) Inventor: Stephan Sattler, Starnberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 389 days.

(21) Appl. No.: 12/266,056

(22) Filed: Nov. 6, 2008

(65) Prior Publication Data

US 2009/0110607 A1 Apr. 30, 2009

Related U.S. Application Data

(63) Continuation of application No. PCT/EP2007/004024, filed on May 7, 2007.

(30) Foreign Application Priority Data

May 8, 2006 (DE) .......... 10 2006 021 404

(51) Int. Cl.
*B01L 3/00* (2006.01)

(52) U.S. Cl. ......... 422/50; 422/68.1; 422/500; 422/501; 422/502; 210/244; 210/255; 210/266; 210/97; 210/98; 210/120; 210/348; 210/472; 210/359; 210/406

(58) Field of Classification Search ............... 422/102, 422/500, 501, 502; 210/224, 225, 226, 97, 210/98, 120, 348, 472, 359, 406, 515, 516, 210/927

See application file for complete search history.

(56) References Cited

U.S. PATENT DOCUMENTS

| | | | |
|---|---|---|---|
| 3,512,940 A | 5/1970 | Shapiro | |
| 4,522,713 A | 6/1985 | Nussbaumer et al. | |
| 4,602,995 A * | 7/1986 | Cassaday et al. | 210/120 |
| 4,683,058 A * | 7/1987 | Lyman et al. | 422/100 |
| 5,102,631 A * | 4/1992 | Jordan et al. | 422/102 |
| 6,221,655 B1 | 4/2001 | Fung et al. | |
| 2004/0157245 A1 | 8/2004 | Radmacher et al. | |

FOREIGN PATENT DOCUMENTS

DE 3838278 C1 1/1990
WO 97/12677 A 4/1997

OTHER PUBLICATIONS

International Preliminary Report on Patentability, Dec. 24, 2008.

* cited by examiner

*Primary Examiner* — In Suk Bullock
*Assistant Examiner* — Sharon Pregler
(74) *Attorney, Agent, or Firm* — Dinsmore & Shohl LLP

(57) ABSTRACT

A liquid container with an upper opening and a tube-shaped withdrawal chimney is disclosed. The withdrawal chimney extends into the container through the upper opening which has a liquid-permeable zone in the form of a finely-porous flow resistance element in its lower end region such that liquid exchange can take place between the withdrawal chimney and the container inner space which surrounds it via the flow resistance element. A venting groove formed by a radial recess of the casing wall of the withdrawal chimney in its upper region may be provided to ensure adequate venting of the space above the liquid level.

10 Claims, 1 Drawing Sheet

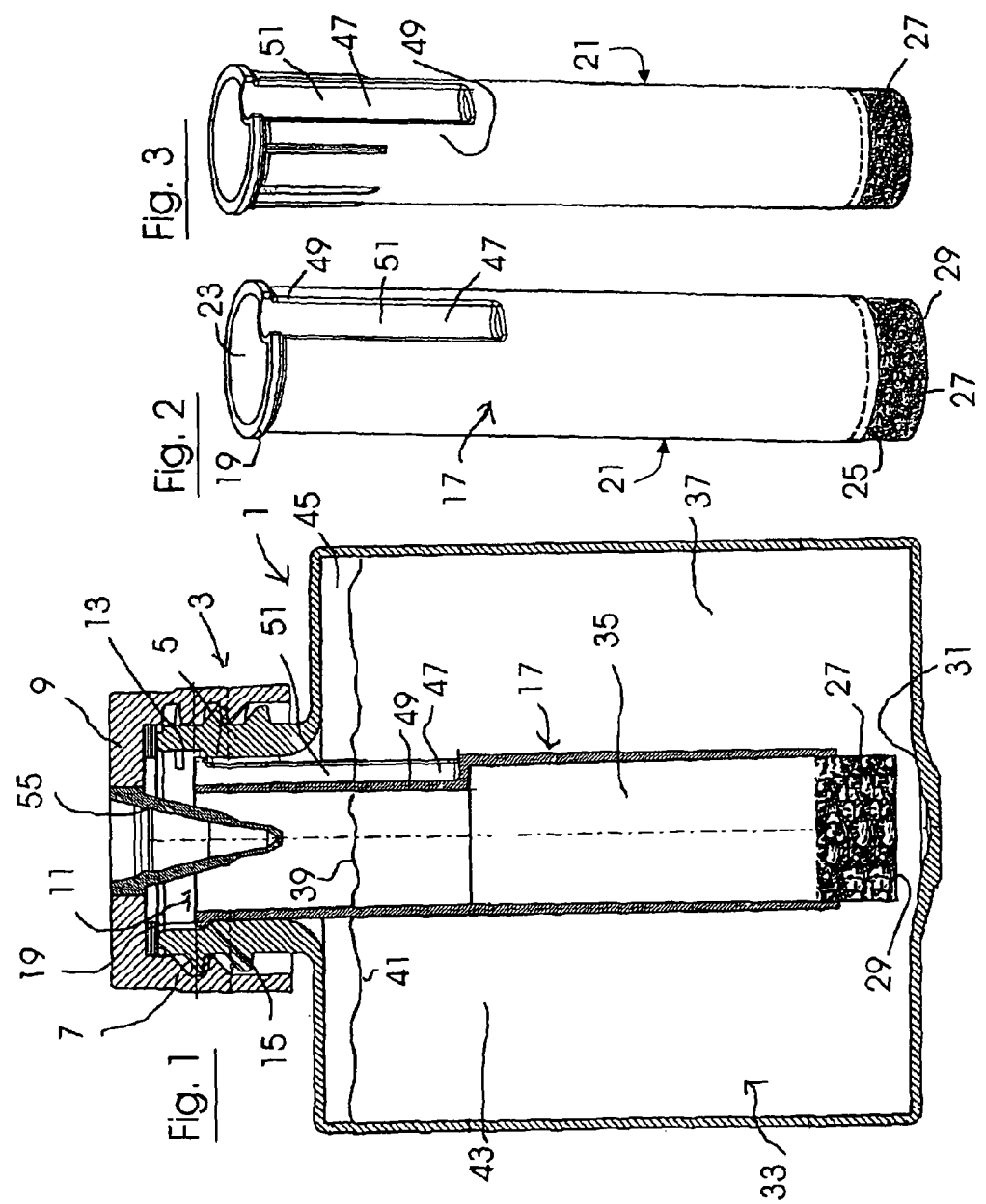

LIQUID CONTAINER WITH AN EXTRACTION CHIMNEY

CROSS REFERENCE TO RELATED APPLICATIONS

This application is a continuation of International Application No. PCT/EP2007/004024 filed May 7, 2007, which claims priority to German Application No. 10 2006 021 404.8, filed May 8, 2006.

FIELD OF THE INVENTION

The present invention relates generally to liquid containers for laboratory use, and in particular to a liquid container with an upper opening and a tube-shaped withdrawal chimney which extends into the container and is flush with the upper opening and which has a liquid-permeable zone in its lower end region near to the bottom of the container.

BACKGROUND OF THE INVENTION

Liquid containers are used as reagent liquid vessels in automated analyzers. When used in such an automated analyzer, reagent liquid is removed from the liquid containers by automatic pipettors. In modern systems this takes place in a rapid cycle in order to enable a high throughput of respective analytical processes. In this process the liquid container is rapidly conveyed to the pipetting station by means of a transport device e.g. in the form of a rotor and is braked there, whereupon the automatic pipette or suction needle dips into the withdrawal chimney through the upper opening of the liquid container in order to remove liquid by suction. In the case of automated analyzers with a high throughput only extremely short cycle times of a few seconds are available for each individual pipetting process including the positioning of the liquid container in the pipetting zone. The problem associated with this is that when the liquid container is abruptly stopped in the pipetting zone, the liquid in the container swashes and may spatter so that a reasonably equalized liquid level often does not occur until after a particular waiting time which takes longer than the required short pipetting cycle time for the high throughput operation. Usually pipetting should be avoided when the liquid level in the withdrawal chimney is still fluctuating because the pipette tip would be wetted on the outside with liquid over a relatively large area in an undesired manner and thus a relatively large entrainment volume of liquid would adhere to the outside of the pipette tip when the pipette is retracted from the liquid container and then cause contaminations in subsequent pipetting operations. In order to avoid this the pipette tip should also only slightly dip into the liquid to be pipetted during pipetting and the fill level in the liquid container should if possible be at rest. Also it should be avoided that the pipette draws air due to a fluctuating liquid level. Furthermore, foam formation in the withdrawal chimney should be suppressed. In the case of previously known liquid containers of the type under consideration here, this requirement can normally only be fulfilled within cycle times which would take too long for high throughput operation in automated analyzers.

Reference can for example be made to WO 97/12677 A1, to U.S. Pat. No. 5,102,631 or to DE 38 38 278 C1 with regard to reaction liquid containers of the prior art with a withdrawal chimney. In the liquid container from WO 97/12677 A1 the upper end of the tube-shaped withdrawal chimney is provided with a radially outwardly projecting flange with which it is supported in a hanging fashion on a spout of the container opening. The completely open lower end of the withdrawal chimney extends into the vicinity of the bottom of the liquid container so that liquid communication can take place through the lower opening of the withdrawal chimney between the withdrawal chimney and the surrounding inner space region of the liquid container. In order to allow the pressure between the inner space of the container and the environment to equalize during pipetting, slot-like reductions in the wall thickness are provided in the upper region of the withdrawal chimney which should enable air to flow in between the opening spout of the liquid container and the casing of the withdrawal chimney.

An embodiment example of a container from DE 38 38 278 C1 has a withdrawal chimney whose cross-section is substantially smaller than the cross-section of the upper container opening and this withdrawal chimney perforates a screw cap screwed onto the opening spout and is attached to this cap. A through-hole in the screw cap allows a pressure equalization between the inner space of the container and the outer environment. The withdrawal chimney reaches the vicinity of the container bottom so that liquid exchange can take place between the withdrawal chimney and the surrounding inner space of the container through the open underside of the withdrawal chimney. In a further embodiment example of DE 38 38 278 C1 the outer circumference of the upper end of the withdrawal chimney and the inner circumference of the spout surrounding the upper end of the withdrawal chimney are only slightly different so that no venting path of sufficient magnitude for pressure equalization between the interior of the container and the environment remains between the outer side of the withdrawal chimney and the inner surface of the spout. A through-bore in the casing of the withdrawal chimney is provided at its upper end for pressure equalization. The lower end of the withdrawal chimney is essentially completely open and spacer bars are provided at the lower end of the withdrawal chimney.

The liquid container known from U.S. Pat. No. 5,102,631 is constructed similarly to the last-mentioned embodiment example from DE 38 38 278 C1 and thus also has a through-hole in the casing of the withdrawal chimney at its upper end. The withdrawal chimney extends to the bottom of the liquid container but large lateral openings are provided in the casing of the withdrawal chimney at its lower end.

Experiments of the inventor on liquid containers of the prior art constructed as elucidated above have confirmed that when the container is rapidly positioned in a treatment zone, the liquid in the container swashes, splatters and may foam in the container and a calmed, equalized level does not occur in the withdrawal chimney until after a period that is not tolerable for high throughput analyzers.

SUMMARY OF THE INVENTION

It is against the above background that the present invention provides an improved liquid container of the type mentioned above which can be used in rapid automated pipetting systems in high throughput operation.

In one embodiment, it is proposed according to the invention that the liquid-permeable zone of the withdrawal chimney has at least one finely-porous flow resistance element so that liquid exchange between the withdrawal chimney and the interior space of the container which surrounds it in the region of the liquid-permeable zone can only take place by way of a respective flow resistance element.

The flow resistance element serves as a flow brake which ensures that when the liquid container is abruptly braked, onsetting swashing movements of the liquid around the withdrawal chimney are considerably damped and are manifested in a delayed manner as slow changes in the level in the withdrawal chimney. Hence, the flow resistance element forms a "low pass" for the liquid in the withdrawal chimney with regard to the frequency and severity of the swashing movements and liquid level oscillations. When the liquid container is rapidly positioned in a pipetting station e.g. by means of a carousel or rotor carrying the container, only relatively slow changes in the level occur in the withdrawal chimney irrespective of the swashing movements around the withdrawal chimney triggered by the stopping of the container. Thus, the pipetting tip of such an automated pipetting device can be admitted into the withdrawal chimney immediately after the container has stopped and dip into the liquid to the smallest possible depth in order to then pipette. The immersion depth or the level of the liquid in the withdrawal chimney is usually detected by sensory means e.g. by means of capacitive sensors in the case of automated pipetting stations and the immersion depth is controlled according to the sensor information. This can be carried out in a corresponding manner also when using a liquid container according to the invention. As desired the pipetting tip is only wetted on its outer side by liquid over a short length so that only a small entrainment volume of liquid can collect on the outside of the pipette. Surprising rapid changes in the level of the liquid in the withdrawal chimney due to the external swashing effect are not to be expected during the short pipetting time due to the low-pass effect of the flow resistance element. The level of liquid in the withdrawal chimney thus at most only varies slowly and to a dampened degree so that the automatic pipetting device can pipette reliably from the respective calculated fill level in the withdrawal chimney with a low immersion depth of the pipette tip.

Furthermore, the flow resistance element can be designed such that it acts as a foam brake which substantially prevents the passage of foam from the inner space of the container into the withdrawal chimney.

The flow resistance element in one embodiment is formed from a fleece material, and in other embodiment, formed from felt or/and a fabric or/and a sintered plastic material, such as for example, polyethylene or polypropylene or/and an open-pored foam.

According to one embodiment of the invention the lower end of the withdrawal chimney has a tube opening on the front end which, however, is filled out with the flow resistance element. In this connection a further development of the invention provides that the flow resistance element projects downwards from the lower opening on the front end of the withdrawal chimney and can thus serve as a spacer element between the bottom of the container and the front end opening of the withdrawal chimney. Such a solution can for example be achieved with a flow resistance element in the form of a filter element made of sintered polyethylene which is inserted and locked in position in the lower opening of the withdrawal chimney.

According to another embodiment of the invention the flow resistance element is a fine-pored grating sieve made of metal or plastic. Alternatively or in addition the withdrawal chimney can be provided with a plurality of capillary through-bores at its lower end and the area of the withdrawal chimney that is finely perforated in this manner forms the flow resistance element. With the diverse possibilities of realizing a flow resistance element, care should always be taken that it offers the desired flow braking property and swashing movements of the liquid can only result in comparatively slow and dampened changes in the level in the withdrawal chimney.

The withdrawal chimney in one embodiment is a component made of plastic which, when preparing the liquid container, can be inserted into the liquid container through its opening.

As is known, it is proposed that the upper opening of the container has a spout which projects upwards and in particular a screw cap spout the inner surface of which forms the circumferential boundary surface of the container opening. The upper end of the withdrawal chimney can have a flange section with which it is attached to an upward facing shoulder face of the spout. The withdrawal chimney can thus be held in a stable manner it its fitting position in the container.

A further aspect of the invention is the provision of a liquid container of the above-mentioned type in which the casing of the withdrawal chimney in the region of its upper end is radially closely adjacent and opposed to the circumferential boundary surface of the container opening and the lower end region of the withdrawal chimney near to the container bottom has a liquid-permeable zone wherein in the area of its upper end the casing wall of the withdrawal chimney is shaped in zones such that in such a zone the outer side of the casing of the withdrawal chimney is at a larger distance from the circumferential boundary surface of the container opening in order to provide a venting path in particular in the form of a venting groove formed by a radial recess in its casing wall which extends axially and downwards beyond the area of the circumferential boundary surface of the container opening.

Such a venting path allows a rapid and effective pressure equalization between the interior of the liquid container and the environment and it can be manufactured in a simple manner. In this connection through-holes in the casing of the withdrawal chimney for venting purposes can be omitted. In the case of liquid containers of the prior art such through-holes require a limitation of the maximum liquid level if it is intended to prevent swashing liquid from entering through the through-opening into the upper region of the withdrawal chimney. It should be noted that the aspect of the venting path is also independently of significance and thus it can also be used for withdrawal chimneys which are not equipped with a flow resistance element of the above-mentioned type but rather with for example a gap of the conventional type.

The invention is further elucidated with reference to the figures.

BRIEF DESCRIPTION OF THE DRAWINGS

FIG. 1 shows in a sectional side-view an embodiment example of a liquid container according to the invention with a withdrawal chimney and flow resistance element in the lower withdrawal chimney opening.

FIG. 2 shows the withdrawal chimney of FIG. 1 separately in a perspective view.

FIG. 3 shows another embodiment of a withdrawal chimney for a liquid container according to the invention in a perspective view.

DETAILED DESCRIPTION

In FIG. 1 an embodiment example of a liquid container 1 according to the invention is shown in a longitudinal section along a vertical centre plane. The liquid container 1 is a bottle with a screw cap 3. The bottle neck 5 is a screw cap spout with an outer thread 7 which serves as a screw thread for the screw cap 9. The spout-like bottle neck 5 has the withdrawal opening 11 of the liquid container 1 and has a shoulder with a ring shoulder 15 which extends radially inwards on its inner surface/circumferential boundary surface 13 on which a withdrawal chimney 17 with an upper end flange 19 is hung.

In FIG. 2 the withdrawal chimney 17 is shown separately in a perspective view. In this example it comprises with regard to its basic form a hollow cylindrical tube body 21 which has tube openings 23, 25 on its front ends. The lower tube opening 25 of the tube body 21 is filled out with a finely-porous flow resistance element 27 which is a liquid-permeable plug made of sintered polyethylene. Other materials may, however, also be used to form the flow resistance element 27 e.g. felt, fabric or open-pored foam. In the example according to FIG. 1 and FIG. 2 the flow resistance element 27 protrudes downwards below the lower edge of the tube body 21 so that it can serve as a spacer element. This function is not utilized in the case of the liquid container in FIG. 1 because the withdrawal chimney 17 is hung in the liquid container 1 in such a manner that the lower end 29 is at a distance, but also small distance, from the bottom 31 of the liquid container 1.

The withdrawal chimney 17 according to FIG. 2 can, however, due to the spacer function of the flow resistance element 27 also be used in liquid containers in which it stands on the bottom of the container.

According to FIG. 1 the withdrawal chimney 17 dips into the container interior 33 down to near the container bottom 31 in the embodiment example shown so that liquid communication between the inner space 35 of the withdrawal chimney 17 and the surrounding ring space 37 in the interior of the container 1 can only take place through the finely-porous flow resistance element 27. In FIG. 1 the liquid container 1 is shown in its resting state in which the liquid level 39 indicated schematically in the withdrawal chimney 17 corresponds to the liquid level 41 in the remaining container space 37.

In acceleration and deceleration processes such as those that occur when the liquid container is transported further and abruptly positioned in a pipetting station, the liquid 43 is, however, set in motion so that it has a tendency to swash, splatter and perhaps foam. This tendency is much greater in the larger ring space area 37 of the container 1 than in the withdrawal chimney 17 with its considerably smaller volume. The flow resistance element 27 ensures that vigorous movements of the liquid in the ring space 37 are not transferred directly to the liquid in the withdrawal chimney but rather occur in a damped and delayed manner so that the level 39 oscillates only relatively slowly even after a rapid positioning of the liquid container 1 in a pipetting station. This can be taken into account in the control of the pipetting process that then takes place. The pipetting process can then be carried out such that the pipetting tip (not shown) that is lowered through the container opening 11 into the withdrawal chimney 17 after removing the cap 9 only dips to a small degree into the liquid 43. The pipetting of the calmed liquid 43 in the withdrawal chimney can thus take place in a very short cycle time of e.g. less than three or even less than two seconds.

In such rapid pipetting operations there is, in addition to the calming of the liquid level 39 in the withdrawal chimney 17, yet a further problem. This further problem concerns the venting of the spatial area 45 above the liquid level 41 during pipetting.

Previous experiments of the inventor with withdrawal chimney constructions that are known from the prior art and have been mentioned above have shown that the venting channels that are possible with these chimneys are too small to enable a sufficiently rapid pressure equalization between the outer space of the container and the spatial area 45 in high throughput operation. An adequately rapid venting would be achieved with a variant of the withdrawal chimney in which a very large window in the withdrawal chimney were to be provided above the liquid level 41. However, such a solution should be avoided according to the invention because such a window in the upper area of the container requires space and therefore limits the maximum fill level of the liquid container. Moreover, there is a risk that liquid 43 may swash in from the ring space 37 into the interior space of the withdrawal chimney 17 through the window so that there is a risk that the pipetting tip introduced into the withdrawal chimney 17 during the pipetting operation is wetted over a large area with the liquid that swashes in.

According to one aspect of the invention which is independently of importance and thus can also be used in withdrawal chimneys without a flow resistance element of the above-mentioned type, the withdrawal chimney 17 has a venting groove 51 formed by a radial recess 47 in its casing wall 49 in the region of its upper end which extends downwards and axially beyond the region of the circumferential boundary surface 13 of the container opening 11 i.e. beyond the region of the spout 5 such that it can provide a sufficiently large and long venting path along the inside of the spout. Such a radial recess 47 of the casing wall 49 of the withdrawal chimney 17 can be manufactured in a simple manner. In particular, but not preferably, several such venting grooves 51 formed by radial recesses can be provided. In the terminology used here radial recess means that the casing wall 49 in the region of the venting groove does not simply have a reduced thickness but rather the shape of the casing wall observed in cross-section describes a radial inwardly projecting recess. In this manner the venting groove can be designed to be comparatively large without impairing the stability of the withdrawal chimney. However, in order to form a venting path it can for example also be provided that the casing wall 49 has a chord-shaped course in a particular zone having an enlarged spacing to the circumferential boundary surface 13 of the container opening 11.

Hence, in the venting design described above it is not necessary to perforate the upper region of the casing wall 49 of the withdrawal chimney 17 with venting windows. Hence the maximum fill level of liquid in the liquid container according to the invention is not limited by venting measures. Also no liquid can reach the inner space 35 of the withdrawal chimney 17 from the ring space 37 in the upper region of the withdrawal chimney 17. Experiments have shown that the tendency of the container liquid to splash out or creep out through the venting groove when the container is accelerated can be counteracted by an optimal orientation of the venting groove 51 in the container 1 relative to its walls and taking into consideration container movement states.

FIG. 3 shows a modified embodiment of the withdrawal chimney 17 from FIG. 1. The tube body 21 of the withdrawal chimney in FIG. 3 has a smaller outer diameter than the tube body in FIG. 1. This is compensated by axially extending spacing ribs 53 on the outside of the cylinder casing wall in the upper region of the withdrawal chimney 17 in FIG. 3 which in the fitted state in the liquid container are opposite to and in close proximity to the inner surface of the screw cap spout and thus ensure that the withdrawal chimney is held in a more stable manner.

Pipetting operations with the liquid container according to the invention usually take place with the closure cap 9 removed. Especially for pipetting operations which may proceed slowly, the closure cap 9 has a guide funnel 55 which, when the closure cap 9 is mounted, can be pierced by the pipette tip when it enters the container 1.

The container 1 according to FIG. 1 can optionally be accommodated together with further containers in a common handling cassette (not shown) in which it can pass through various stations in an automated analyzer.

In a variant of the embodiment example shown, a liquid container according to the invention can also be designed as a two-chamber container or multichamber container having several withdrawal chimneys of the aforementioned type.

What is claimed is:

1. A liquid container having a bottom and an upper opening with a circumferential boundary surface and comprising:
    a tube-shaped withdrawal chimney which extends into the container and is in flush with the upper opening, said withdrawal chimney has an upper end region, a lower end region and a casing wall and comprises
    a liquid permeable opening at the lower end region of the withdrawal chimney and near to the bottom of the container,
    an outer circumference at its upper end region radially closely adjacent and opposed to the circumferential boundary surface of the upper opening, and
    a venting groove in the upper end region of the withdrawal chimney, said venting groove being formed by a radially inwardly projecting recess of the casing wall and extending axially and downwards beyond the circumferential boundary surface of the container opening,
    wherein the withdrawal chimney is configured to communicate with its surrounding space within the container via the liquid permeable opening so as to provide for liquid exchange between the withdrawal chimney and its surrounding space within the container in order to equalize the liquid level within the container, when said container contains liquid.

2. The liquid container according to claim 1, wherein the upper opening of the container has a screw cap spout which projects upwards and has an inner surface which forms the circumferential boundary surface of the container opening.

3. The liquid container according to claim 2, wherein the upper end region of the withdrawal chimney has a flange section which is attached to an upward facing shoulder surface of the spout.

4. The liquid container according to claim 3, wherein the shoulder surface of the spout that faces upwards is provided in the inner surface of the spout.

5. The liquid container according to claim 1, wherein the liquid permeable opening has at least one finely-porous flow resistance element so that liquid exchange between the withdrawal chimney and an interior space of the container, which surrounds the withdrawal chimney in the region of the liquid permeable opening, can only take place by way of the respective flow resistance element.

6. The liquid container according to claim 5, wherein the at least one flow resistance element is formed from a fleece material, felt, a fabric, a sintered plastic material, polyethylene, polypropylene, an open-pored foam, and combinations thereof.

7. The liquid container according to claim 5, wherein the at least one flow resistance element is a fine-pored grating sieve or a lower wall section of the withdrawal chimney with a plurality of capillary through-bores.

8. The liquid container according to claim 5, wherein the withdrawal chimney has an opening at its lower front end which is filled out with the at least one flow resistance element.

9. The liquid container according to claim 8, wherein the at least one flow resistance element projects downwards out of the opening of the withdrawal chimney.

10. The liquid container according to claim 1, wherein the withdrawal chimney comprises a tube element that can be inserted into the liquid container through the opening.

* * * * *